US011995825B2

(12) United States Patent
Weiss (10) Patent No.: US 11,995,825 B2
(45) Date of Patent: May 28, 2024

(54) METHOD FOR MOTION ARTIFACT DETECTION (71) Applicant: KONINKLIJKE PHILIPS N.V., Eindhoven (NL)

(72) Inventor: Steffen Weiss, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 389 days.

(21) Appl. No.: 17/613,101

(22) PCT Filed: May 25, 2020

(86) PCT No.: PCT/EP2020/064376
§ 371 (c)(1),
(2) Date: Nov. 22, 2021

(87) PCT Pub. No.: WO2020/239661
PCT Pub. Date: Dec. 3, 2020

(65) Prior Publication Data
US 2022/0215540 A1 Jul. 7, 2022

(30) Foreign Application Priority Data
May 28, 2019 (EP) .................................... 19176878

(51) Int. Cl.
*G06T 7/00* (2017.01)
(52) U.S. Cl.
CPC .. *G06T 7/0012* (2013.01); *G06T 2207/10088* (2013.01); *G06T 2207/20081* (2013.01); *G06T 2207/20084* (2013.01)

(58) Field of Classification Search
CPC ........... G06T 5/30; G06T 5/90; G06T 7/0012; A61B 5/055; A61B 5/0263; G01R 33/5676
See application file for complete search history.

(56) References Cited

U.S. PATENT DOCUMENTS 8,724,881 B2 * 5/2014 Zheng ..................... G06T 7/149
382/131
9,811,924 B2 * 11/2017 Johnson ................ G06T 11/003
(Continued)

FOREIGN PATENT DOCUMENTS

WO 2019086284 A1 5/2019

OTHER PUBLICATIONS

Kudo et al "Estimation of Static Field Inhomogeneity and Patient Motion in Magnetic Resonance Imaging" Systems and Computers in Japan 1990 (only abstract and JP language version).
(Continued)

*Primary Examiner* — Yosef Kassa (57) ABSTRACT

The present disclosure relates to a medical imaging method for motion artifact detection. The method comprises: using (201-203) a k-space acquisition property for generating a motion-corrupted image having a motion artifact as caused by a first initial motion pattern such that the motion artifact is defined as function of a feature matrix and the motion-corrupted image; initializing (205) at least one feature map of a convolutional neural network, CNN, with values of the convolution matrix; training (207) the initialized CNN to obtain, in training images, motion artifacts caused by a second training motion pattern; obtaining (209) a motion artifact in an input image using the trained CNN.

15 Claims, 6 Drawing Sheets

(56) References Cited

U.S. PATENT DOCUMENTS

| | | | |
|---|---|---|---|
| 10,074,037 B2 * | 9/2018 | Lu | A61B 8/58 |
| 10,092,199 B2 * | 10/2018 | Heberlein | G01R 33/5676 |
| 10,324,153 B2 * | 6/2019 | Li | G01R 33/5615 |
| 10,698,063 B2 * | 6/2020 | Braun | G06T 5/73 |
| 2018/0374245 A1 | 12/2018 | Xu et al. | |

OTHER PUBLICATIONS

G. A. Wright, "Magnetic resonance imaging," in IEEE Signal Processing Magazine, vol. 14, No. 1, pp. 56-66, Jan. 1997, doi: 10.1109/79.560324.

M. Zaitsev, et al., "Motion artifacts in MRI: A complex problem with many partial solutions" JMRI 42:887-901, 2015.

Sommer K, et al. "Correction of Motion Artifacts Using a Multi-Resolution Fully Convolutional Neural Network" ISMRM2018, #1175.

Liu et al "Reducing Streaking Artifacts in Quantitative Susceptibility Mapping Via Deep Learniing" International Soc. for Magnetic Reson. in Med. No. 5001 Jun. 1, 2018.

International Search Report and Written Opinion from PCT/EP2020/064376 dated Dec. 3, 2020.

* cited by examiner

METHOD FOR MOTION ARTIFACT DETECTION

CROSS REFERENCE TO RELATED APPLICATIONS

This application is a U.S. national phase application of International Application No. PCT/EP2020/064376 filed on May 25, 2020, which claims the benefit of EP Application Serial No. 19176878.7 filed on May 28, 2019 and is incorporated herein by reference.

FIELD OF THE INVENTION

The invention relates to scanning imaging systems, in particular to a method for motion artifact detection in an input image.

BACKGROUND OF THE INVENTION

During a magnetic resonance imaging (MRI) scan, radio frequency (RF) pulses generated by a transmitter antenna cause perturbations to the local magnetic field, and RF signals emitted by the nuclear spins are detected by a receiver antenna. These RF signals are used to construct MR images. During a longer scan, the scanned subject can have an internal or external motion which corrupts the data and results in MR images with blurs or artifacts. Numerous methods have been proposed to mitigate or correct for MR motion artifacts. These methods; however, operate in image-space and try to recognize the specific features of motion artifacts based on affected images.

SUMMARY OF THE INVENTION

Various embodiments provide for a method for motion artifact detection in an input image, medical analysis system, and computer program product, as described by the subject matter of the independent claims. Advantageous embodiments are described in the dependent claims.

Motion artifacts are one of the most frequent causes of image degradation in MRI. Deep learning (DL) techniques may be applied to motion-correction of MR images by, for example, applying DL networks in image-space after conventional MR image reconstruction. However, these techniques may discard the explicit information on the k-space sampling pattern and its timing. Some but not all of this information is implicitly learned during training of the convolutional kernels of the DL network after being initialized by noise values. This may require a considerable effort and large amounts of training data. The present subject matter may further improve the motion correction by using the explicit knowledge of the sampling pattern and its timing in order to design DL networks and to initialize their kernels such that they are pre-trained to estimate common motion artifacts such as translational motion artifacts. An algorithm may be used to calculate these kernels, with low efforts, directly from sequence parameters and predefined motion paths. This initialization may considerably shorten the effort for training, which is performed to address other forms of motion.

In one aspect, the invention relates to a medical imaging method for motion artifact detection. The method comprises: using a k-space acquisition property for generating a motion-corrupted image having a motion artifact as caused by a first initial motion pattern such that the motion artifact is a function of a feature matrix and the motion-corrupted image; initializing at least one feature map of a convolutional neural network, CNN, with values of the feature matrix; training the initialized CNN with training images, the training images being corrupted by a second pattern (type) of motion to obtain motion artifacts; obtaining a motion artifact in an input image using the trained CNN. The first initialising type of motion and the second motion pattern are fairly approximated by (multiple) displacements. The accuracy of the approximation of the initial motion pattern (the first initialising type of motion) and the motion pattern of the image to be corrected for artefacts (the second training type of motion (pattern)) depends on the predetermined level of residual artifacts associated with a pre-set required image quality.

The present subject matter enables to guide the network to learn the pure properties of the artifacts rather than also anatomical properties. The CNN is initialized for motion correction using image features of MR motion artifacts in order to reduce the training effort. The obtained motion artifact may for example be used to correct motion artifacts in the input image. This may increase the accuracy of the artifact detection and thus of MR motion correction. The present subject matter may enable an automatic correction of motion artifacts in magnetic resonance images.

The present subject matter may prevent loss of artifact information by using the k-space acquisition property. In particular, the present subject matter takes into account the fact that any motion due to a consecutive acquisition patterns in k-space translates to a time-coherence of motion corruption in k-space, that these patterns are much more difficult to "learn" by convolutional networks in the image domain, and that the explicit knowledge on the time-coherence is lost during Fourier reconstruction.

For example, the trained CNN may be accessible by a remote computer system (e.g. the trained CNN may be stored in the computer system), wherein the computer system is configured to: upon receiving an MR image to automatically detect the motion artifact in the MR image using the trained CNN. This may be advantageous as it may enable a centralized and consistent artifact detection e.g. among different MRI systems, using the trained CNN.

The k-space acquisition property may be determined dependent on an MR imaging protocol. The imaging protocol or protocol refers to a set of technical settings or set of acquisition parameters of imaging modalities to produce the images (e.g. MR images) required for an examination. For example, an acquisition parameter may indicate a pulse sequence type. For example, the method comprises providing a given MR imaging protocol, wherein the k-space acquisition property may be determined using the given MR imaging protocol. The k-space property may be determined by k-space sampling pattern and its timing. A set of subject displacements dx(t) may be chosen so that it reflects typical realistic motions (e.g. of the first type), e.g. with constant velocity in any direction, fast displacements to a new position after an initial still period, oscillations, or more complex motions. The maximum amplitude of dx(t) may be much smaller than the field of view (FOV) of the image as in a clinical imaging set-up. All choices for dx(t) may comply with the laws of mechanics, e.g. be continuous and two-times differentiable functions of time. This may be advantageous as it may further increase the accuracy of the artifact detection by using consistent data acquisition settings while allowing the motion induced artifacts to be different. And, the training may enable to learn artifacts of rotational and non-rigid-body motion.

According to one embodiment, the initializing comprises: for each feature map of the CNN determining the feature matrix with a different first initial motion pattern, and initializing said feature map using the values of the feature matrix.

For example, every assumed type of motion results in an individual feature matrix. This embodiment enables to initialize individual kernels (or feature maps) of parallel kernels of the CNN using individual motions. Preferentially, large motions may be assigned to lowly resolved kernels, and vice versa small motions to highly resolved kernels. For example, the first initial motion pattern is determined based on the resolution of the kernel to be initialized. If the kernel to be initialized has a resolution higher than a predefined resolution threshold, the first initial motion pattern may have a motion amplitude or shift that is smaller than a predefined motion amplitude threshold. If the kernel to be initialized has a resolution smaller than the predefined resolution threshold, the first initial motion pattern may have a motion amplitude or shift that is higher than the predefined motion amplitude threshold. In another example, for each resolution of the kernel of the CNN, a respective first motion type may be defined and used for defining the motion artifact. This may enable an accurate motion artifact detection as the CNN are initialized in an accurate manner on an individual basis.

According to one embodiment, the motion artifact is defined in k-space as a multiplication of the feature matrix and the motion-corrupted image, wherein the feature map is a multiplicative layer of the CNN and the CNN is configured to receive as input the k-space representation of images. This embodiment may enable to implement the CNN to operate entirely in k-space (the CNN has Fourier Transform (FT) layers) and be fed directly with the measured data, corresponding to the FT of the measured images. The CNN of this embodiment may comprise multiplicative layers instead of convolutional kernels.

According to one embodiment, the motion artifact is defined in image space as a convolution of the feature matrix and the motion-corrupted image, wherein the feature map is a kernel of the CNN, and the CNN is configured to receive as input images. This embodiment may enable to implement the CNN to operate entirely in image-space and be fed directly with the measured images. The CNN of this embodiment may comprise convolutional kernels.

In a further embodiment, the CNN may include FT layers and $FT^{-1}$ layers representing k-space and image space respectively, wherein features maps of each layer of the CNN are initialized using the feature matrix obtained in the corresponding space. The CNN may then enable to switch between image-space and k-space in subsequent layers of the CNN.

According to one embodiment, the first initial motion pattern is a translation motion characterized by a respective translational displacement. This embodiment may be advantageous because translational motion may be a good first approximation of all present motion during MR scanning. Thus, the effort and amount of training for this type of motion may be reduced by the present subject matter. In particular the present subject matter may reduce or save the efforts involved in the two following cases: 1) Calculation of training data usually involves simulation of motion artifacts for vast amounts of individual images, involving FT, k-space data manipulation, and inverse FT per image. 2) Actual training may also require considerable effort to "teach" the convolutional kernels step by step using random subsets of the training images.

According to one embodiment, the second training motion pattern is a combination of first initial motion patterns, wherein each first initial motion pattern is characterized by a respective translational displacement.

According to one embodiment, the motion artifact in the input image is induced a by a motion which is a combination of the first initial motion pattern and the second training motion pattern; or the second training motion pattern.

According to one embodiment, the motion of the first type is different from or is the same as the motion of the second type. The second training motion pattern may be a combination of different first initial motion patterns.

According to one embodiment, the k-space acquisition property comprises the pattern of sampling and/or timing of sampling of the k-space. The present subject matter may for example use the explicit knowledge of the sampling pattern and its timing to design and initialize the CNN such that it is set-up and pre-trained to estimate translational motion artifacts in an image. The CNN may further be trained to address rotational and more complex motions. This is by contrast to another method operating entirely in image-space resulting in a loss of at least part of the information on the k-space sampling pattern and its timing. There is a structure and information that may not be exploited with this other method e.g. because of the fact that the probability that two sampling points in k-space represent the same motion state declines continuously with their distance in sampling time. Even introducing implicit knowledge of the pattern and its timing into the network during the training of the other method it may not be sufficient or efficient as it is indirect and thus inefficient and it may not exploit all available information.

According to one embodiment, the motion artifact A of the motion corrupted image M is defined as a convolution of the motion corrupted image M with the feature matrix K, wherein the feature matrix K is defined by $$K = FT^{-1}\left(\frac{FT(D-\delta)}{FT(D)}\right),$$

wherein A=M⊗

$$FT^{-1}\left(\frac{FT(D-\delta)}{FT(D)}\right) = M \otimes K, D = FT^{-1}\left[e^{-i(\vec{k}d\vec{x}(t(\vec{k})))}\right],$$

δ is a delta function, dx(t) is a motion function, and FT stands for Fourier transform, k is a k-space position of the motion corrupted image M.

According to one embodiment, the motion artifact A of the motion corrupted image M is defined in k-space as a multiplication of the motion corrupted image M in k-space with the feature matrix, wherein the feature matrix is defined by $$\frac{FT(D-\delta)}{FT(D)},$$

wherein $$FT(A) = FT(M)\frac{FT(D-\delta)}{FT(D)}, D = FT^{-1}\left[e^{-i(\vec{k}d\vec{x}(t(\vec{k})))}\right],$$

δ is a delta function, dx(t) is a motion function, and FT stands for Fourier transform, k is a k-space position of the motion corrupted image M.

The CNN of this embodiment may comprise multiplicative layers instead of convolutional kernels which may be initialized with the feature matrix $$\frac{FT(D-\delta)}{FT(D)},$$

as derived from the properties of k-space, such as k-space sampling pattern and its timing, and specific motions.

According to one embodiment, the k-space representation is a two or three dimensional representation.

According to one embodiment, the method further comprises receiving the input image from a magnetic resonance imaging, MRI, system, the method being performed during operation of the MRI system. This may enable an online or real-time artifact correction method.

A further aspect of the invention pertains to training of a convolutional neural network including a separate initialisation of its kernels (feature map) and training of the CNN. Training of the CNN according to the invention requires less effort and or time as compared to conventional training. Subsequently, the trained CNN may be employed in motion correction of magnetic resonance images.

In another aspect, the invention relates to a computer program product comprising machine executable instructions for execution by a processor, wherein execution of the machine executable instructions causes the processor to the methods of any of the preceding embodiments.

In another aspect, the invention relates to a medical analysis system, the medical imaging system comprising at least one processor; and at least one memory including computer program code; the at least one memory and the computer program code configured to, with the at least one processor, cause the medical imaging system at least to perform at least part of the method of any of the preceding embodiment.

The medical analysis system is configured to connect to multiple MRI systems and to receive the input image from an MRI system of the MRI systems.

In another aspect, the invention relates to an MRI system comprising the medical analysis system. The MRI system is configured for acquiring image data and to reconstruct initial images out of the image data, the initial images being processed by the medical analysis system to perform at least part of the method of any of the preceding claims.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figures are either similar elements or perform an equivalent function. Elements which have been discussed previously will not necessarily be discussed in later figures if the function is equivalent.

Various structures, systems and devices are schematically depicted in the figures for purposes of explanation only and so as to not obscure the present invention with details that are well known to those skilled in the art. Nevertheless, the attached figures are included to describe and explain illustrative examples of the disclosed subject matter.

Figure 1:
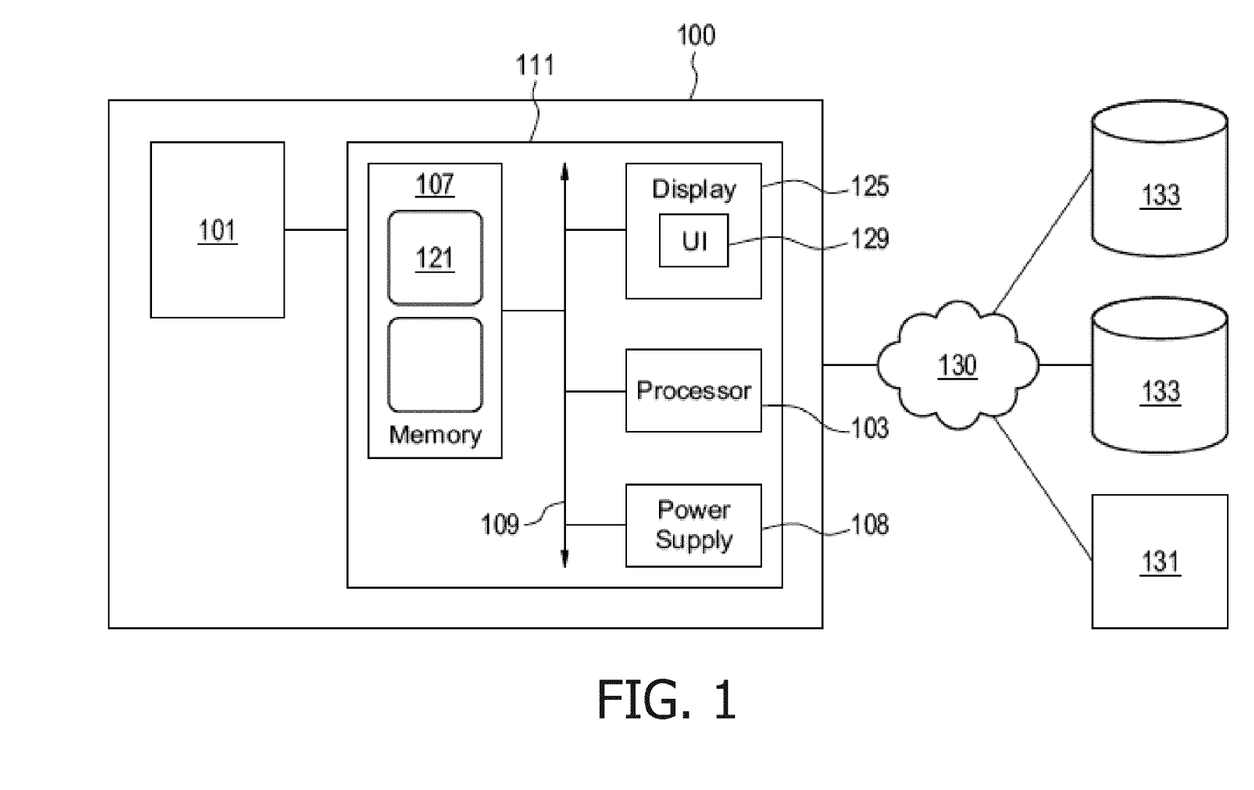
FIG. 1 is a schematic diagram of a medical analysis system.

FIG. 1 is a schematic diagram of a medical analysis system 100. The medical analysis system 100 comprises a control system 111 that is configured to connect to a scanning imaging system (or acquisition component) 101. The control system 111 comprises a processor 103, a memory 107 each capable of communicating with one or more components of the medical system 100. For example, components of the control system 111 are coupled to a bidirectional system bus 109.

It will be appreciated that the methods described herein are at least partly non-interactive, and automated by way of computerized systems. For example, these methods can further be implemented in software 121, (including firmware), hardware, or a combination thereof. In exemplary embodiments, the methods described herein are implemented in software, as an executable program, and is executed by a special or general-purpose digital computer, such as a personal computer, workstation, minicomputer, or mainframe computer.

The processor 103 is a hardware device for executing software, particularly that stored in memory 107. The processor 103 can be any custom made or commercially available processor, a central processing unit (CPU), an auxiliary processor among several processors associated with the control system 111, a semiconductor based microprocessor (in the form of a microchip or chip set), a micro-processor, or generally any device for executing software instructions. The processor 103 may control the operation of the scanning imaging system 101.

The memory 107 can include any one or combination of volatile memory elements (e.g., random access memory (RAM, such as DRAM, SRAM, SDRAM, etc.)) and non-volatile memory elements (e.g., ROM, erasable programmable read only memory (EPROM), electronically erasable programmable read only memory (EEPROM), programmable read only memory (PROM). Note that the memory 107 can have a distributed architecture, where various components are situated remote from one another, but can be accessed by the processor 103. Memory 107 may store an instruction or data related to at least one other constituent element of the medical analysis system 100.

The control system 111 may further comprise a display device 125 which displays characters and images and the like e.g. on a user interface 129. The display device 125 may be a touch screen display device.

The medical analysis system 100 may further comprise a power supply 108 for powering the medical analysis system 100. The power supply 108 may for example be a battery or an external source of power, such as electricity supplied by a standard AC outlet.

The scanning imaging system 101 may comprise at least one of MRI, CT and PET-CT imagers. The control system 111 and the scanning imaging system 101 may or may not be an integral part. In other terms, the control system 111 may or may not be external to the scanning imaging system 101.

Figure 7:
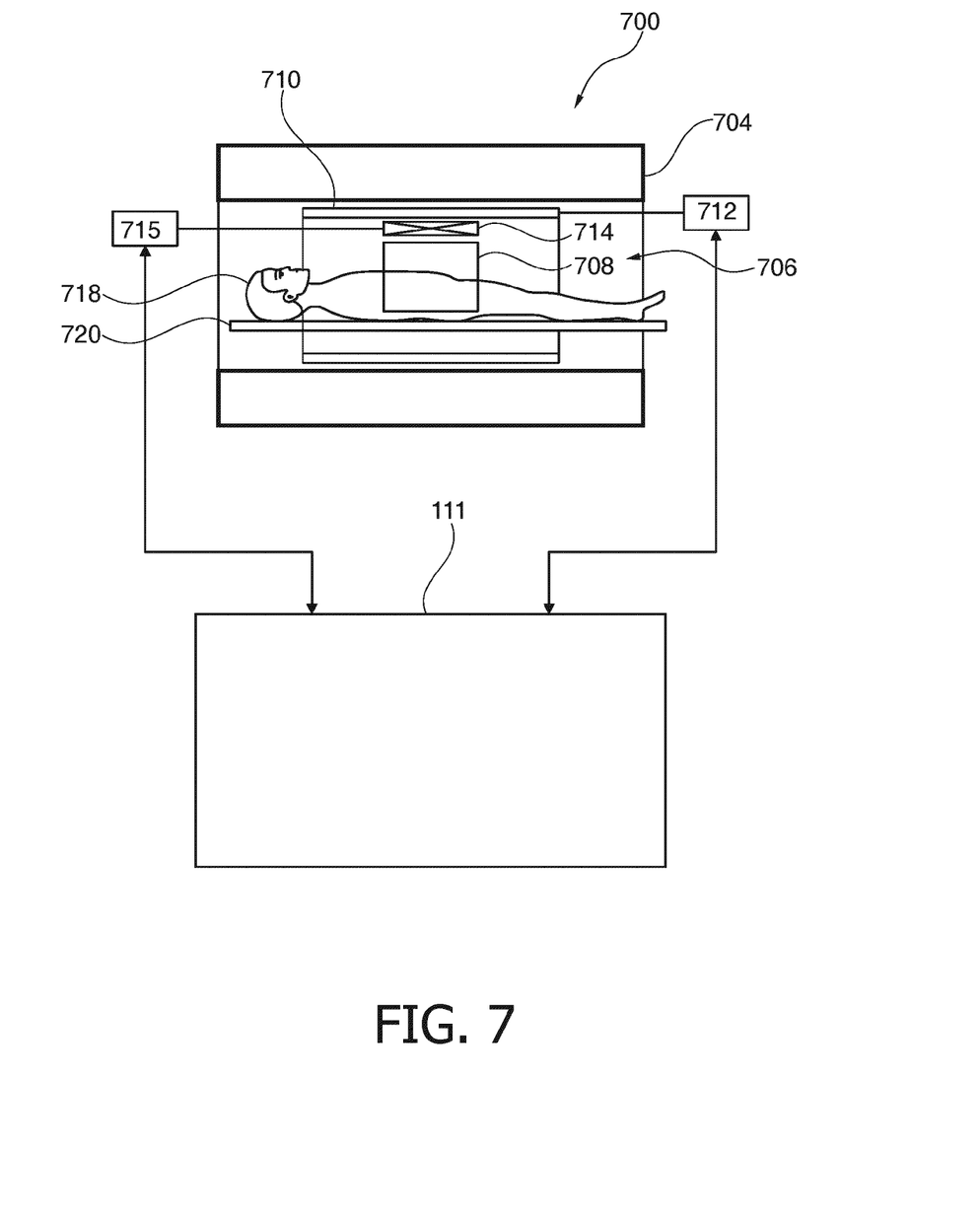
FIG. 7 shows a cross-sectional and functional view of an MRI system.

The scanning imaging system 101 comprises components that may be controlled by the processor 103 in order to configure the scanning imaging system 101 to provide image data to the control system 111. The configuration of the scanning imaging system 101 may enable the operation of the scanning imaging system 101. The operation of the scanning imaging system 101 may for example be automatic. FIG. 7 shows an example of components of the scanning imaging system 101 being an MRI system.

The connection between the control system 111 and the scanning imaging system 101 may for example comprise a BUS Ethernet connection, WAN connection, or Internet connection etc.

In one example, the scanning imaging system 101 may be configured to provide output data such as images in response to a specified measurement. The control system 111 may be configured to receive data such as MR image data from the scanning imaging system 101. For example, the processor 103 may be adapted to receive information (automatically or upon request) from the scanning imaging system 101 in a compatible digital form so that such information may be displayed on the display device 125. Such information may include operating parameters, alert notifications, and other information related to the use, operation and function of the scanning imaging system 101.

The medical analysis system 100 may be configured to communicate via a network 130 with other scanning imaging systems 131 and/or databases 133. The network 130 comprises for example a wireless local area network (WLAN) connection, WAN (Wide Area Network) connection LAN (Local Area Network) connection or a combination thereof. The databases 133 may comprise information relates to patients, scanning imaging systems, anatomies, scan geometries, scan parameters, scans etc. The databases 133 may for example comprise an EMR database comprising patients' EMR, Radiology Information System database, medical image database, PACS, Hospital Information System database and/or other databases comparing data that can be used for planning a scan geometry. The databases 133 may for example comprise training images. Additionally or alternatively the training images may be stored in a local storage (e.g. disk storage or memory) of the control system 111.

The memory 107 may further comprise an artificial intelligence (AI) component 150. The AI component 150 may or may not be part of software component 121. The AI component 150 may be configured for training a CNN in accordance with the present subject matter and to provide the trained CNN for further use. For example, if the control system 111 is not part of the scanning imaging system 101, the trained CNN may be provided to the scanning imaging system 101 such that it can be used at the scanning imaging system 101 for detecting artifacts in images that are reconstructed by the scanning imaging system 101.

Figure 2:
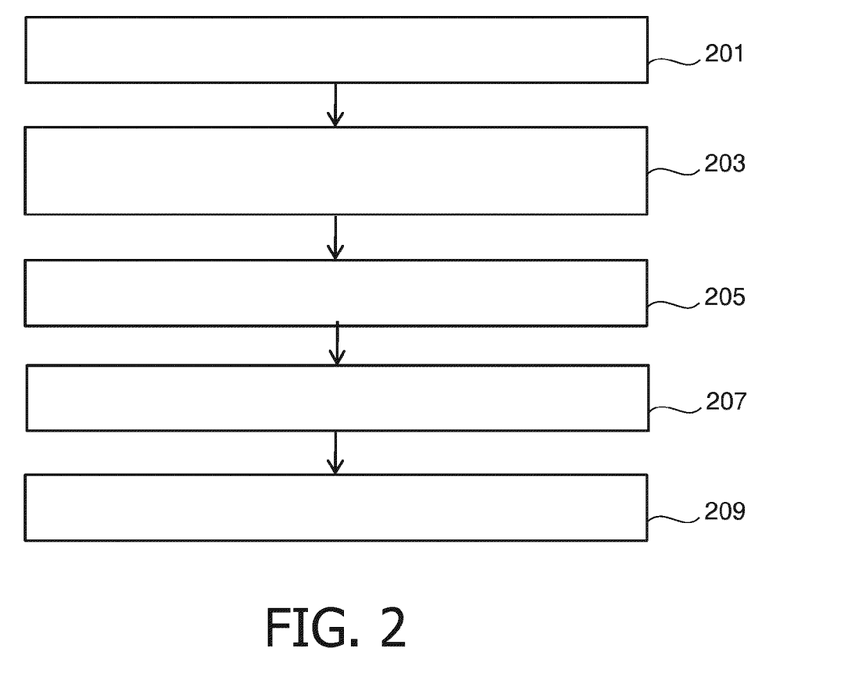
FIG. 2 is a flowchart of a medical imaging method for motion artifact detection.

FIG. 2 is a flowchart of a medical imaging method for motion artifact detection. A motion corrupted image M may be obtained in step 201. The motion corrupted image may be a modelled or simulated image e.g. this may be performed starting from an ideal image having no motion artifact. The motion corrupted image may result from a given k-space acquisition property. The k-space acquisition property may for example comprise a sampling pattern x and its timing t. One or more shift functions $dx(t)$ describe a first initial motion pattern. The first initial motion pattern may be a translational displacement function $dx(t)$ where t may include all times when k-space is sampled. The motion corrupted image has a known motion artifact that is caused by the first initial motion pattern.

The motion artifact A may be defined or modelled in step 203 as function of a feature matrix and the motion-corrupted image M. The motion artifact A may be defined in k-space and/or image space. In one example, the motion artifact A of the motion corrupted image M may be modelled in image space as a convolution of the motion corrupted image M with the feature matrix. In this case the feature matrix is a convolution matrix. In another example, the motion artifact A of the motion corrupted image M may be modelled in k-space as a multiplication of the motion corrupted image M with the feature matrix. In this case the feature matrix is a multiplicative matrix.

In one example, for each feature map of a CNN, steps 201 and 203 may be repeated using a different first initial motion pattern. This may result in each feature map of the CNN being associated with a respective feature matrix. The difference between the first initial motion patterns of these matrices may be defined based for example on the resolution of the feature maps. For example, large motions may be assigned to lowly resolved feature maps, and vice versa small motions to highly resolved feature maps.

At least one feature map of the CNN may be initialized in step 205 with values of the feature matrix. In one example, each filter kernel of the CNN may be initialized with the values of the feature matrix. This may enable an improved training of the CNN and thus an improved accuracy of artifact detection. In another example, each filter kernel of the first layer of the CNN may be initialized with the values of the feature matrix. This may further improve the training of the CNN and the accuracy of artifact detection. In another example, for each filter kernel of the CNN, steps 201-205 may be repeated for different first type motions, resulting in each filter kernel being initialized by a respective feature matrix. For example, multiple motion corrupted images may be obtained using different hypothetical shift functions $dx(t)$, and respective feature matrices may be determined. This may further improve the training of the CNN and the accuracy of artifact detection. In one example, the feature maps of the CNN may have respective predefined sizes. In another example, the size of each feature map of the CNN may be defined using the first initial motion pattern used for initializing the feature map. This may enable that the feature map is not larger in a first direction (e.g. x direction) than the extent of the first initial motion pattern, and in a second direction (e.g. y direction) the size of the feature map is governed by the k-space timing and acquisition pattern. This is for example shown in the image representing "kernel K" in FIGS. 5 and 6, where the white pixels of the images can be used to determine the size of the feature map to be initialized by that "kernel K". For example, equation (8) calculates K at full resolution for a given motion and then downsizes it to the relevant support such that it corresponds to the size of the feature map. The downsized version may be used to initialize that feature map of the CNN.

The initialized CNN may be trained in step 207 to obtain, in training images, motion artifacts caused by a second training motion pattern. Each of the training images has a motion artifact that is caused by the second training motion pattern. In one example, the second training motion pattern may be a combination of multiple first initial motion patterns, wherein each first initial motion pattern is characterized by a respective translational displacement. This may improve the training of the CNN and the accuracy of artifact detection since the initialization already takes into account at least part of the motion in the training images. The training may converge quickly by using such initialization method.

Using the trained CNN, a motion artifact may be obtained from an input image in step 209.

The obtaining of the motion artifact may for example comprise: determining using the CNN if the input image has a motion artifact and if it has the motion artifact, the motion artifact may be obtained using the values provided by the trained CNN. For example, the trained CNN may provide as output a number of pixel values, wherein each pixel value is indicative of the motion artifact content at that pixel location, which may be zero or vanishing. In other terms, the CNN may take measured motion-corrupted images as input and estimate the pure motion artifact as output. The pure artifact may be subtracted from the measured image to yield a corrected image. The motion artifact detection may be accurate using the trained CNN as it is initialized using values that reflect real motions that unusually occur during MR imaging. This may particularly be advantageous if the motion artifact in the input image is induced by a motion which is a combination of the first initial motion pattern and the second training motion pattern; or which is the second training motion pattern.

Figure 3:
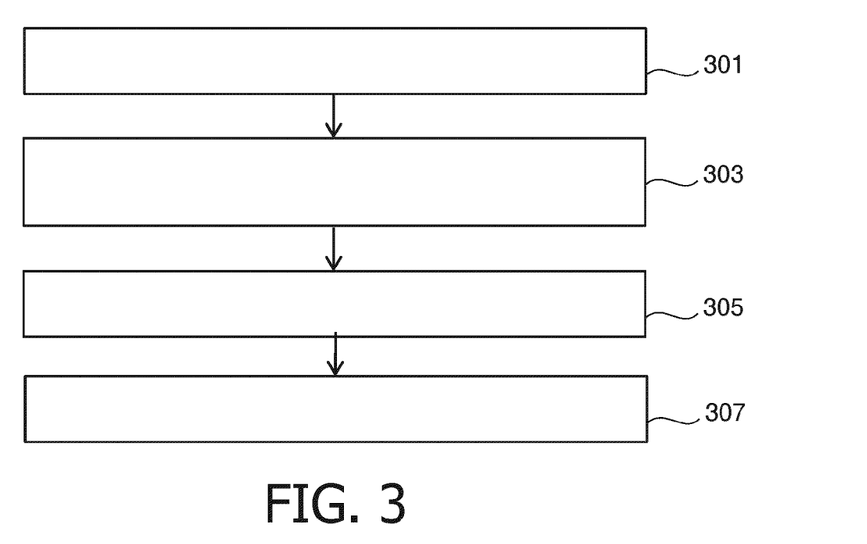
FIG. 3 is a flowchart of a method for determining a convolution matrix in accordance with an example of the present subject matter.

FIG. 3 is a flowchart of a method for determining a convolution matrix in accordance with an example of the present subject matter.

Assuming, for example, that an ideal image I with its k-space data S=FT(I) is subject to a motion characterized by a translational displacement function dx(t) where t includes all times when k-space is sampled. The motion corrupted image M may be determined or defined in step 301 as follows: $M(\vec{x}) = \int S(\vec{k}) e^{-i(\vec{k}(\vec{x}+\vec{dx}(t(\vec{k}))))} d\vec{k} = \int S(\vec{k}) E(\vec{k}) e^{-i(\vec{k}\vec{x})} d\vec{k}$ (1), where E is an exponential phase term.

The motion corrupted image of equation (1) may be defined in step 303 as function of a kernel D that yields to the image M from the ideal image I. This may be performed as follows using equations (2) to (3).

$$E(\vec{k}) = e^{-i(\vec{k}\vec{dx}(t(\vec{k})))} \quad (2)$$

If the inverse FT of E is denoted as D=FT$^{-1}$(E), and ⊗ is the convolution, then M can be written as $$M = FT^{-1}[SE] = FT^{-1}[FT(I)E] \quad (3)$$

$$= I \otimes FT^{-1}(E) = I \otimes D \quad (3')$$

D is the inverse FT of the exponential phase term E defined by k-space sampling pattern, its timing, and the motion. If A is the pure artifact within the motion corrupted image M, and δ the delta function, then the pure artifact A may be defined in step 305 using the image M as follows.

$$A = M - I \quad (4)$$

$$= I \otimes D - I = I \otimes (D - \delta)$$

$$= (M - A) \otimes (D - \delta)$$

$$= MD(D - \delta) - A \otimes (D - \delta)$$

$$= M \otimes (D - \delta) - A \otimes D + A \quad (4').$$

This results in $A \otimes D = M \otimes (D - \delta)$ (5)

The convolution matrix may be determined in step 307 by first applying of the Furrier transform to equation (5) using convolution theorem. This results in equations (6)

$$FT(A)FT(D) = FT(M)FT(D - \delta) \quad (6)$$

$$FT(A) = FT(M)\frac{FT(D - \delta)}{FT(D)} (6'),$$

and by second applying an inverse FT to equation (6') using convolution theorem. This results in equation (7).

$$A = M \otimes FT^{-1}\left(\frac{FT(D - \delta)}{FT(D)}\right) = M \otimes K, \quad (7)$$

$$\text{with } K = FT^{-1}\left(\frac{FT(D - \delta)}{FT(D)}\right). \quad (8)$$

Equation (8) provides a modelling of the convolution matrix K. The convolution matrix K in image space is the kernel that may be used to yield the pure artifact per convolution with measured images. Since kernel D is the inverse FT of the exponential phase term E which depends on k-space sampling pattern, its timing, and the motion, the convolution matrix K may depend also solely on these properties.

The convolution matrix K of equation (8) may be determined separately for combinations of each motion and each imaging protocol. For example, the motion type is defined by values of dx(t), while the sampling pattern and timing are defined by the set of acquisition parameters (e.g. by the type of the acquisition) of the imaging protocol.

Figure 4:
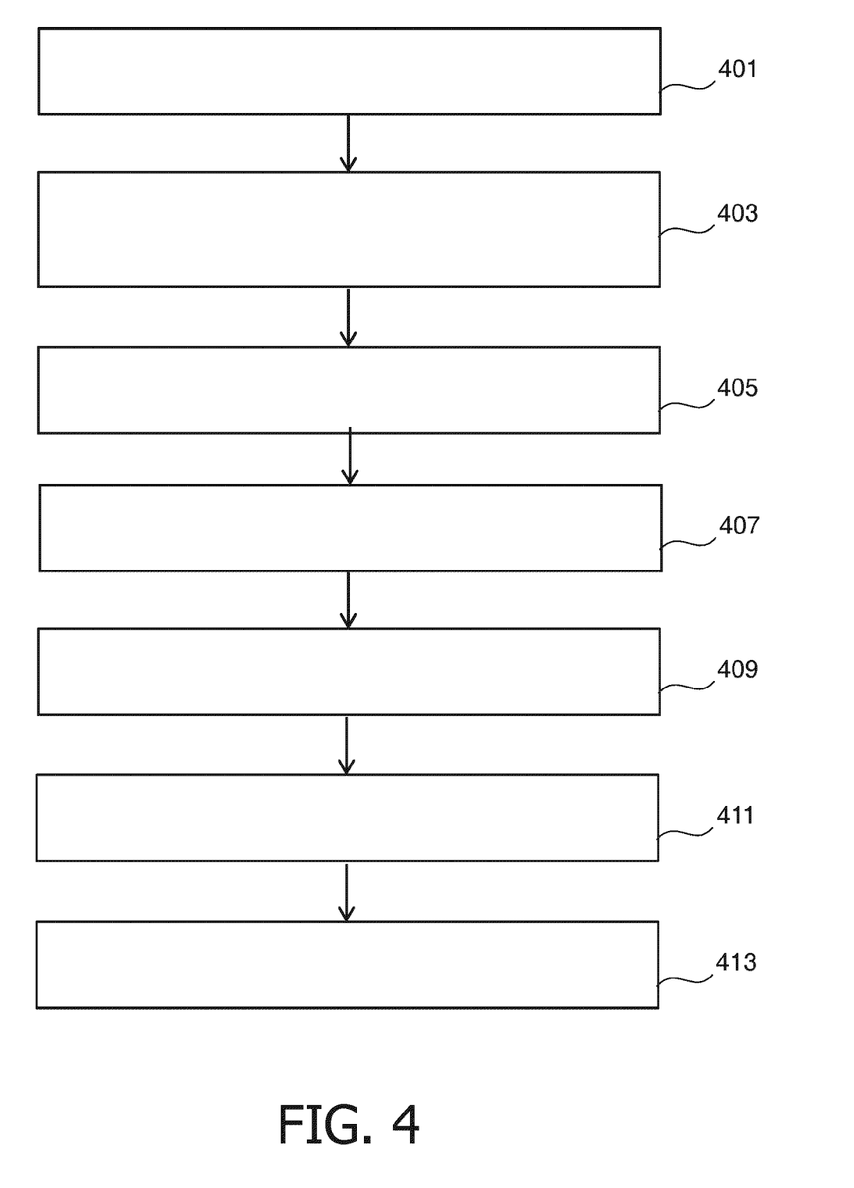
FIG. 4 is a flowchart of a method for validating the convolution matrix determination method in accordance with an example of the present subject matter.
Figure 5:
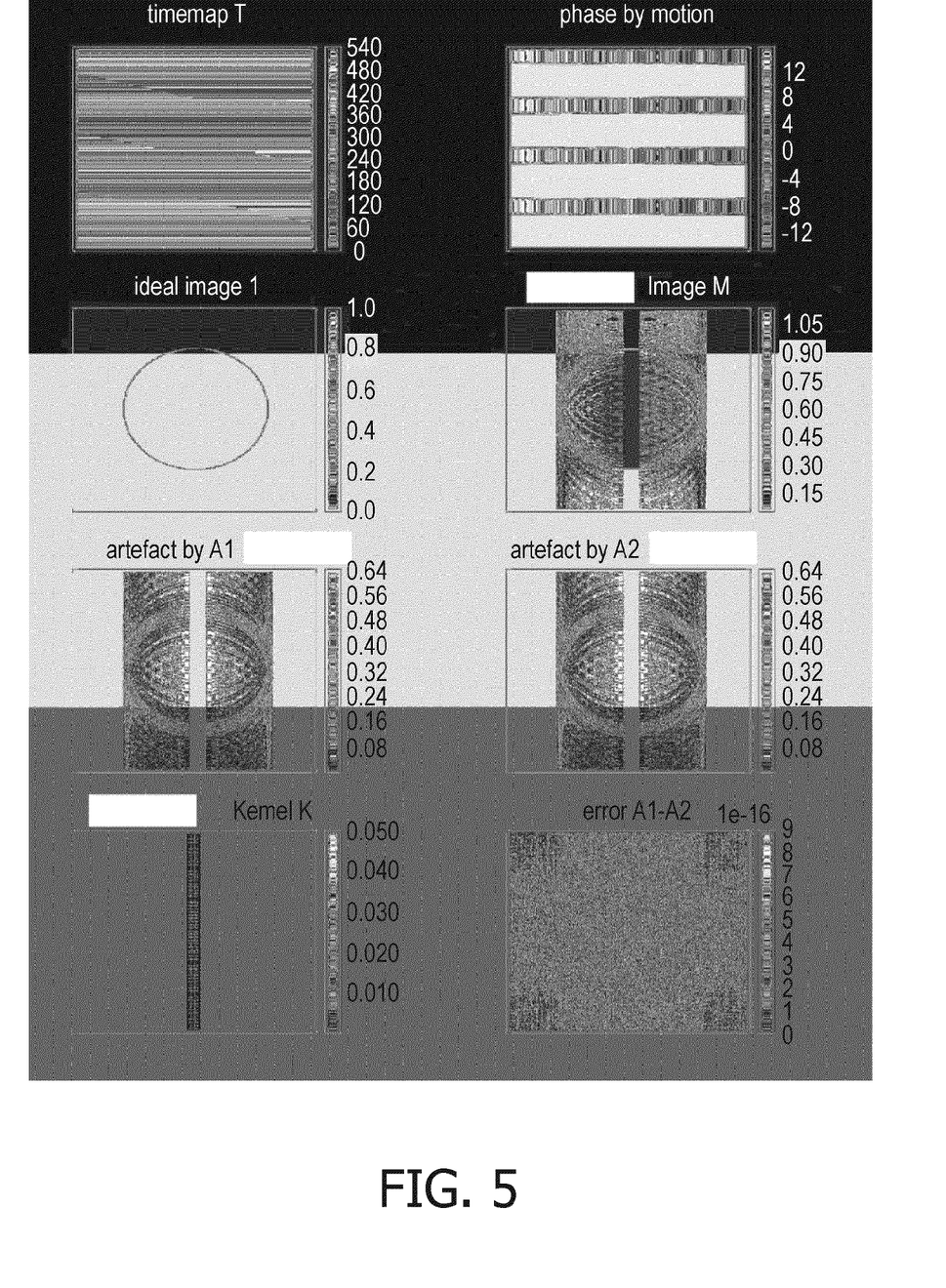
FIG. 5 depicts images illustrating a method for detecting artifacts in accordance with the present subject matter.
Figure 6:
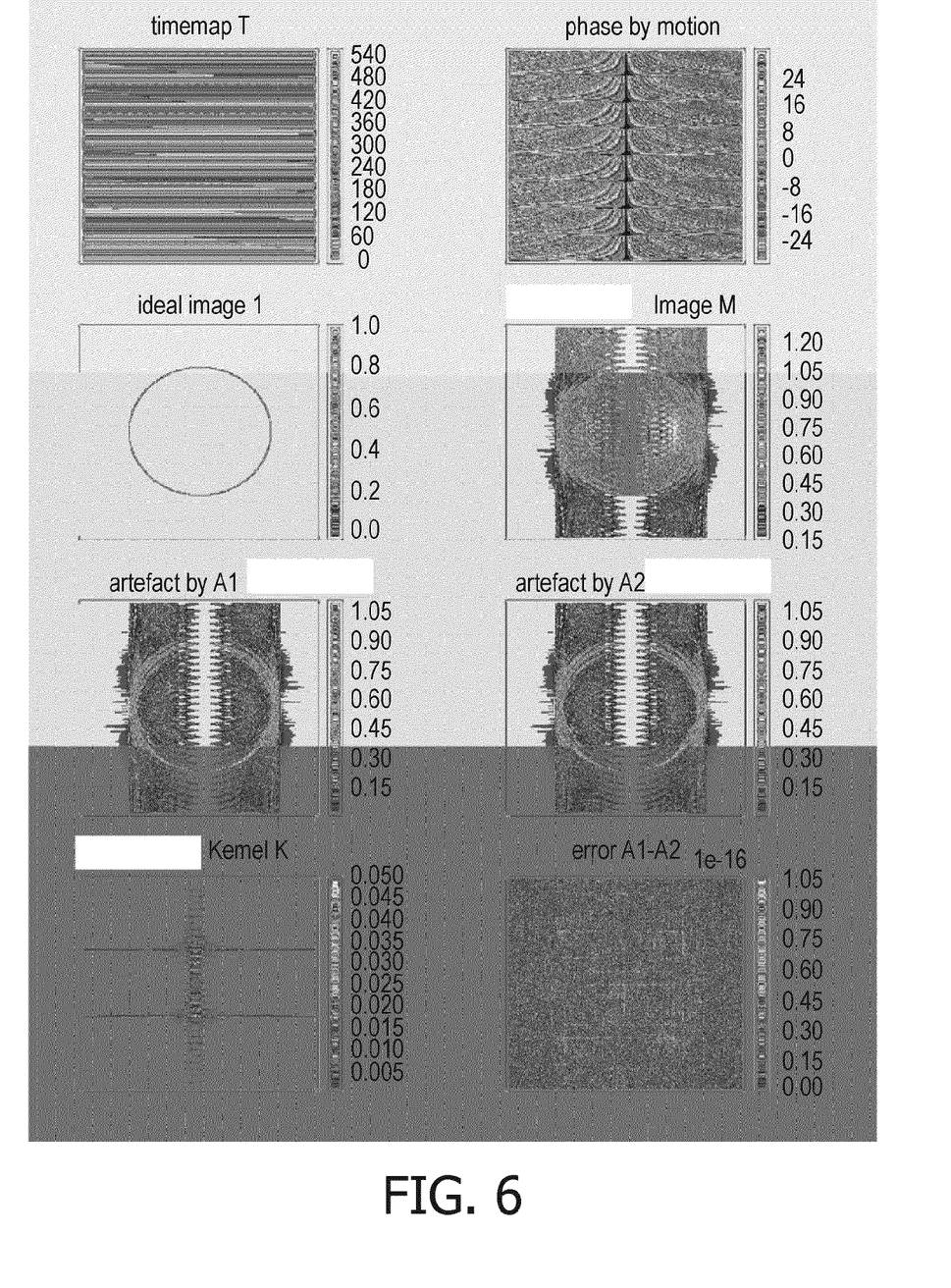
FIG. 6 depicts images illustrating a method for detecting artifacts in accordance with the present subject matter.

FIG. 4 is a flowchart of a method for checking or validating the method of FIG. 3. FIG. 4 may use examples of acquisitions that include the motion as incorporated in equation (8). For that, an ideal phantom image I holding a circular disk is used to simulate motion-corrupted images M. And, selected specific motions dx(t) were assumed to take place during acquisition with a turbo field echo sequence with a typical turbo-factor, sampling pattern and timing. The method of FIG. 4 may for example include the following steps for each motion and set of sequence parameters. In step 401, a time map T, that assigns the time of sampling to each point in k-space based on the sequence type and parameters, is calculated. In step 403, a map of phases induced in k-space by the motion dx(t) is calculated using the exponent in equation (2). In step 405, the motion-corrupted image M is calculated using equations (2) and (3). In step 407, the ground truth artifact A1 is calculated by subtracting the ideal phantom image I from M. In step 409, the convolution matrix K used for initialisation of the CNN is calculated using equation (8). In step 411, the pure artifact A2 is calculated using the convolution matrix K and equation (7). In step 413, the difference of A2 from ground truth A1 is calculated to assess the accuracy of equations (7) and (8) and thus of the method of FIG. 3. FIGS. 5 and 6 show the images obtained as described with steps of FIG. 4.

FIG. 5 depicts the results of the checking method based on a TFE sequence with segmented Cartesian k-space acquisition (resolution 256², TR 9 ms, turbo factor 4, inter-echo-time 2 ms). A sudden displacement in readout direction of 5 pixels after acquisition of 70% of the k-space data was assumed. As shown in FIG. 5, the time map visualizes the 4-fold segmentation in k-space. The phase map shows a flat phase for 70% of the data and a linear phase in readout direction with increasing slope in phase encoding direction due to the displacement for the rest of the data. The pure artifact A2 calculated using the convolution matrix K is almost identical to the artifact A1 calculated by subtracting the ideal image I from the measured image M e.g. by MRI system 700. The convolution matrix K shows two rows of pixels, displaced by 5 pixels resembling the prescribed motion.

FIG. 6 displays data for turbo factor 8 (TR 17 ms, inter-echo-time 2 ms) and a continuous motion by 10 pixels in readout direction. The convolution matrix K resembles this motion by 10 pixel long horizontal lines, now spaced further apart vertically due to the higher segmentation. An additional motion of 5 pixels in phase encoding direction was added.

In the examples of FIGS. 5 and 6, the convolution matrix K mainly resembles the motion path, which is replicated in phase encoding direction in a way that depends on the specific sampling pattern. In all examples, the error for calculation of the artifact using the kernel is negligible, which proofs the correctness of equations (7) and (8).

FIG. 7 illustrates a magnetic resonance imaging system 700 as an example of the medical system 100. The magnetic resonance imaging system 700 comprises a magnet 704. The magnet 704 is a superconducting cylindrical type magnet with a bore 706 in it. The use of different types of magnets is also possible; for instance, it is also possible to use both a split cylindrical magnet and a so called open magnet or a sealed magnet. A split cylindrical magnet is similar to a standard cylindrical magnet, except that the cryostat has been split into two sections to allow access to the iso-plane of the magnet. Such magnets may for instance be used in conjunction with charged particle beam therapy. An open magnet has two magnet sections, one above the other with a space in-between that is large enough to receive a subject 718 to be imaged, the arrangement of the two sections area similar to that of a Helmholtz coil. Inside the cryostat of the cylindrical magnet there is a collection of superconducting coils. Within the bore 706 of the cylindrical magnet 704 there is an imaging zone or volume or anatomy 708 where the magnetic field is strong and uniform enough to perform magnetic resonance imaging.

Within the bore 706 of the magnet there is also a set of magnetic field gradient coils 710 which is used during acquisition of magnetic resonance data to spatially encode magnetic spins of a target volume within the imaging volume or examination volume 708 of the magnet 704. The magnetic field gradient coils 710 are connected to a magnetic field gradient coil power supply 712. The magnetic field gradient coils 710 are intended to be representative. Typically, magnetic field gradient coils 710 contain three separate sets of coils for the encoding in three orthogonal spatial directions. A magnetic field gradient power supply supplies current to the magnetic field gradient coils. The current supplied to the magnetic field gradient coils 710 is controlled as a function of time and may be ramped or pulsed.

MRI system 700 further comprises an RF coil 714 at the subject 718 and adjacent to the examination volume 708 for generating RF excitation pulses. The RF coil 714 may include for example a set of surface coils or other specialized RF coils. The RF coil 714 may be used alternately for transmission of RF pulses as well as for reception of magnetic resonance signals e.g., the RF coil 714 may be implemented as a transmit array coil comprising a plurality of RF transmit coils. The RF coil 714 is connected to one or more RF amplifiers 715.

The magnetic field gradient coil power supply 712 and the RF amplifier 715 are connected to a hardware interface of control system 111. The memory 107 of control system 111 may for example comprise a control module. The control module contains computer-executable code which enables the processor 103 to control the operation and function of the magnetic resonance imaging system 700. It also enables the basic operations of the magnetic resonance imaging system 700 such as the acquisition of magnetic resonance data.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a 'circuit', 'module' or 'system'. Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

A 'computer memory' or 'memory' is an example of a computer-readable storage medium. A computer memory is any memory which is directly accessible to a processor. A 'computer storage' or 'storage' is a further example of a computer-readable storage medium. A computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising 'a processor' should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the 'C' programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks. A 'user interface' as used herein is an interface which allows a user or operator to interact with a computer or computer system. A 'user interface' may also be referred to as a 'human interface device'. A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word 'comprising' does not exclude other elements or steps, and the indefinite article 'a' or 'an' does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
101 scanning imaging system
103 processor
107 memory
108 power supply
109 bus
111 control system
121 software
125 display
129 user interface
150 AI component
201-413 method steps
700 magnetic resonance imaging system
704 magnet
706 bore of magnet
708 imaging zone
710 magnetic field gradient coils
712 magnetic field gradient coil power supply
714 radio-frequency coil
715 RF amplifier
718 subject.

The invention claimed is:

1. A method for motion artifact detection in an input image, comprising:
using a k-space acquisition property representing a k-space sampling pattern and its timing for generating a motion-corrupted image having a motion artifact as caused by a first initialising type of motion pattern such that the motion artifact is defined as function of a feature matrix representing motion induced corrupted encodings and the motion-corrupted image;
initializing at least one feature map representing a convolutional neural network's convolutional or multiplicative kernels with values of the feature matrix;
training the initialized convolutional neural network (CNN) with training images, the training images being corrupted by a second training motion pattern pattern to obtain motion artifacts;
obtaining a motion artifact in an input image using the trained CNN.

2. The method of claim 1, wherein the initializing comprises for each feature map of the CNN determining the feature matrix with a different first initialising type of motion pattern, and initializing said feature map using the values of the feature matrix.

3. The method of claim 1, wherein the motion artifact is defined in k-space as a multiplication of the feature matrix and the motion-corrupted image, wherein the feature map is a multiplicative layer of the CNN and the CNN is configured to receive as input the k-space representation of images.

4. The method of claim 1, wherein the motion artifact is defined in image space as a convolution of the feature matrix and the motion-corrupted image, wherein the feature map is a kernel of the CNN, and the CNN is configured to receive as input images.

5. The method of claim 1, the first initialising type of motion being a translation motion characterized by a respective translational displacement.

6. The method of claim 1, the second type motion being a combination of first initial motion pattern, wherein each first initial motion pattern is characterized by a respective translational displacement.

7. The method of claim 1, wherein the motion artifact in the input image is induced a by a motion which is
a combination of the first initial motion pattern and the second training motion patternsecond training motion pattern; or
the second training motion patternsecond training motion pattern.

8. The method of claim 1, wherein the first initial motion pattern is different from or is the same as the second training motion patternsecond training motion pattern.

9. The method of claim 1, the k-space acquisition property comprising the pattern of sampling and/or timing of sampling of the k-space.

10. The method of claim 1, wherein the motion artifact A of the motion corrupted image M is defined as a convolution of the motion corrupted image M with the feature matrix K, wherein the feature matrix K is defined by $$K = FT^{-1}\left(\frac{FT(D-\delta)}{FT(D)}\right),$$

wherein $$A = M \otimes FT^{-1}\left(\frac{FT(D-\delta)}{FT(D)}\right) = M \otimes K, D = FT^{-1}\left[e^{-i\left(\vec{k}\vec{dx}(t(\vec{k}))\right)}\right],$$

δ is a delta function, dx(t) is a motion function, and FT stands for Fourier transform, k is a k-space position of the motion corrupted image M.

11. The method of claim 1, wherein the motion artifact A of the motion corrupted image M is defined in k-space as a multiplication of the motion corrupted image M in k-space with the feature matrix, wherein the feature matrix is defined by $$\frac{FT(D-\delta)}{FT(D)},$$

wherein $$FT(A) = FT(M)\frac{FT(D-\delta)}{FT(D)}, D = FT^{-1}\left[e^{-i(\vec{k}\vec{dx}(n(\vec{k})))}\right],$$

δ is a delta function, dx (t) is a motion function, and FT stands for Fourier transform, k is a k-space position of the motion corrupted image M.

12. A method for training an convolutional neural network (CNN) for motion artifact detection, comprising:
  using a k-space acquisition property representing a k-space sampling pattern and its timing for generating a motion-corrupted image having a motion artifact as caused by a first initialising type of motion pattern such that the motion artifact is defined as function of a feature matrix representing motion induced corrupted encodings and the motion-corrupted image;
  initializing at least one feature map representing a convolutional neural network's convolutional or multiplicative kernels with values of the feature matrix;
  training the initialized convolutional neural network (CNN) with training images, the training images being corrupted by a second training motion pattern pattern to obtain motion artifacts.

13. A computer program product comprising machine executable instructions stored on a non-transitory computer readable medium for execution by a processor, wherein execution of the machine executable instructions causes the processor to perform the method of claim 1.

14. A medical analysis system, the medical analysis system comprising at least one processor; and at least one memory including computer program code; the at least one memory (103) and the computer program code configured to, with the at least one processor, cause the medical analysis system at least to perform the method of claim 1.

15. A magnetic resonance imaging (MRI) system comprising:
  a medical analysis system including at least one processor; and at least one memory including computer program code; the at least one memory and the computer program code configured to, with the at least one processor, cause the medical analysis system to perform a method for motion artifact detection in an input image, the method including:
  using a k-space acquisition property representing a k-space sampling pattern and its timing for generating a motion-corrupted image having a motion artifact as caused by a first initialising type of motion pattern such that the motion artifact is defined as function of a feature matrix representing motion induced corrupted encodings and the motion-corrupted image;
  initializing at least one feature map representing a convolutional neural network's convolutional or multiplicative kernels with values of the feature matrix;
  training the initialized convolutional neural network (CNN) with training images, the training images being corrupted by a second training motion pattern pattern to obtain motion artifacts; and
  obtaining a motion artifact in an input image using the trained CNN.

* * * * *